United States Patent [19]

Graham

[11] Patent Number: 4,827,615

[45] Date of Patent: May 9, 1989

[54] MICROSURGERY SAW DRIVE

[76] Inventor: Gregory S. Graham, 972 Waterbury La., Ventura, Calif. 93001

[21] Appl. No.: 26,038

[22] Filed: Mar. 16, 1987

[51] Int. Cl.⁴ .................. B23D 57/00; F16H 21/18; A61B 11/00

[52] U.S. Cl. .................................. 30/166 R; 30/219; 30/392; 74/48; 74/50; 128/317

[58] Field of Search ................ 74/47, 48, 50; 30/217, 30/218, 219, 220, 166 R, 392; 128/310, 317

[56] References Cited

U.S. PATENT DOCUMENTS

| | | | |
|---|---|---|---|
| 1,481,055 | 1/1924 | Fullbright | 74/50 |
| 1,556,547 | 10/1925 | Ricard | 74/50 |
| 2,439,262 | 4/1948 | Nalbach et al. | 74/48 |
| 2,455,655 | 12/1948 | Carroll | 128/317 |
| 2,547,707 | 4/1951 | Karle | 128/317 |
| 3,044,171 | 7/1962 | Cecere | 128/317 |
| 3,269,197 | 8/1966 | Enders | 74/50 |
| 3,554,197 | 1/1971 | Dobbie | 128/317 |
| 3,973,378 | 8/1976 | Bartasevich et al. | 30/218 |
| 4,071,029 | 1/1978 | Richmond et al. | 128/310 |

FOREIGN PATENT DOCUMENTS 719969 4/1942 Fed. Rep. of Germany ...... 128/317
12397 6/1896 United Kingdom .................. 30/219

OTHER PUBLICATIONS

Ho Chow, "Linkages-The Why & How", *Mechanisms, Linkages & Mechanical Controls*, McGraw-Hill 1965, pp. 348-349.

Primary Examiner—Allan D. Herrmann
Attorney, Agent, or Firm—Grant L. Hubbard

[57] ABSTRACT

A microsurgery saw comprising drive means for producing rotary motion, rotary-to-lateral converting means operatively driven by the drive means, saw support means for pivotally supporting a microsurgery saw operatively connected to the converting means for transmitting lateral drive motion to the microsurgery saw, drive casing means surrounding and positioning the drive means and saw support casing means surrounding and positioning the saw support means is disclosed.

12 Claims, 4 Drawing Sheets

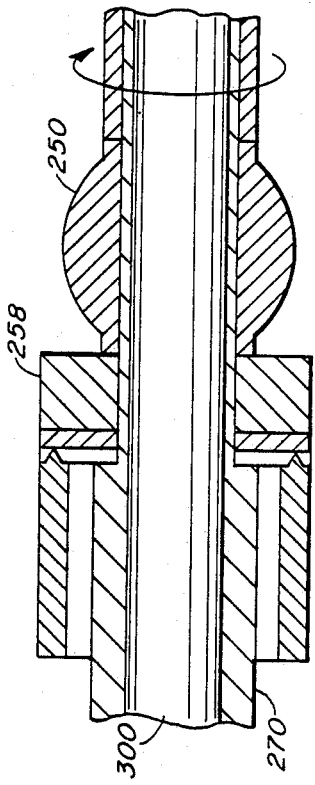
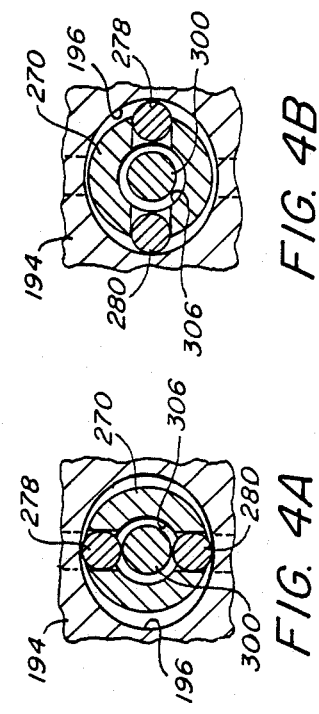
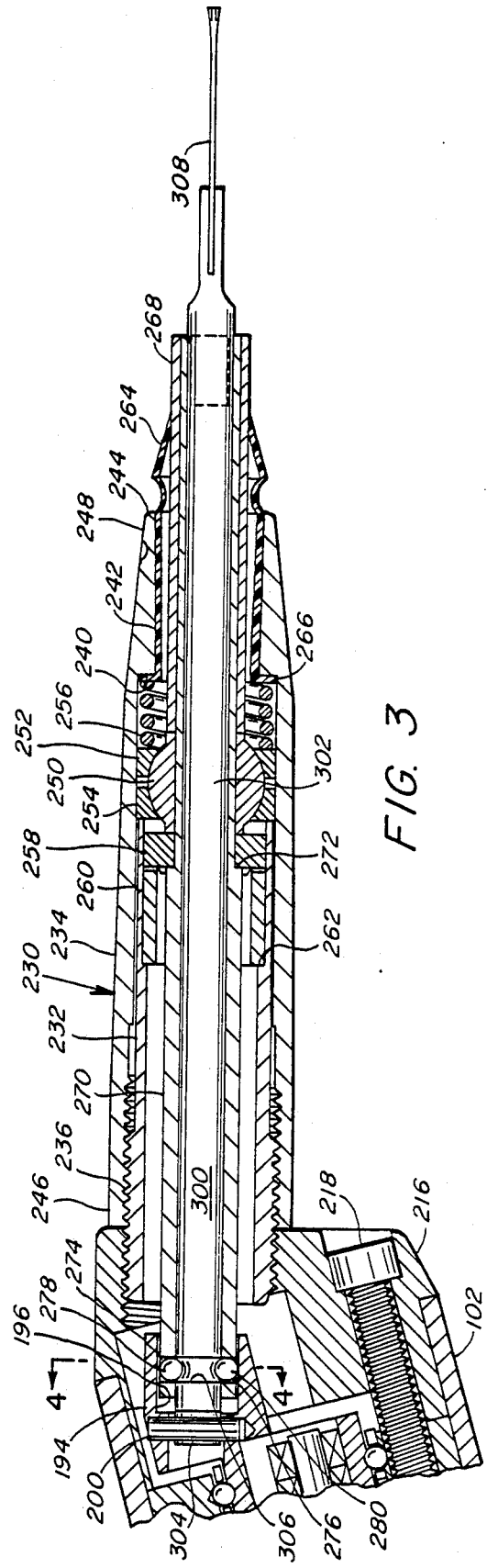

MICROSURGERY SAW DRIVE

FIELD OF THE INVENTION

This invention relates to surgical apparatus generally and specifically to apparatus for performing surgery on small bony and related structures such as, for example, the cervical vertebrae.

BACKGROUND OF THE INVENTION

Microsurgical techniques are often very important in correcting diseased or damaged bone or other structure without the trauma of normal surgical techniques. For example, fusion of vertebrae of the spinal column is indicated in many cases of diseased or damaged vertebrae. There are several well-known procedures for performing vertebrae fusions and the techniques are generally described in voluminous literature on the subject. These general procedures are of limited applicability in treating diseases or injuries to the cervical vertebrae. Cervical vertebrae are delicate, with small bodies, and a very large neural canal. Consequently, the available bone is limited and many procedures which may be quite satisfactory in treating thoracic and lumbar vertebrae, which are much larger, are not applicable in the treatment of cervical vertebrae. One could cite other microsurgical techniques, such as are used in certain joint surgical procedures, etc.

A feature of this invention is in the provision of a small, easily handled microsurgery saw drive for operating a delicate micro-saw in microsurgical procedures generally, e.g. in cervical vertebrae fusion procedures, and in other procedures where it is necessary or desirable to make small cuts in bone or rigid body structures. The drive of this invention is designed for use, most advantageously, with the microsurgery saw described herein, but is not so limited.

SUMMARY OF THE INVENTION

The present invention includes, in one facet, a rotary-to-lateral motion converting assembly comprising concentric-eccentric rotor so constructed and arranged as to form a central main rotor portion, a proximal concentric drive shaft portion and an eccentric distal drive shaft portion. A motor, which is conveniently an electric motor but may be fluid driven, or of any other type, is operably connected to the concentric-eccentric rotor for rotating the same. An eccentric drive shaft of the concentric-eccentric rotor engages a way block mounted for reciprocal, lateral travel. The eccentric drive shaft portion is so disposed and constructed as to engage the lateral way block for driving the same in response to drive power from the motor reciprocally laterally to thereby convert the rotary motion of the motor through the concentric-eccentric rotor to lateral motion of the way block.

The way block comprises, in a preferred but not required form, a generally rectangular main block portion having formed thereon ways which are constructed and disposed to movably support the way block for lateral movement in a plane generally perpendicular to the axes of the concentric-eccentric rotor. The way block is also preferably constructed and configured to define a generally oval aperture in the main block portion for receiving the eccentric shaft of the concentric-eccentric rotor. The aperture formed and configured to define side walls which are operably engaged alternately by the eccentric shaft portion thereof first on one wall for moving the way block (180) in one direction laterally and then on the other wall for moving the way block in the other direction laterally.

The mechanism is designed, in the preferred but not required embodiment, to drive a microsurgical saw, such as, for example, a cervical saw. In this embodiment, the way block also comprises saw engaging means for moving the proximal end of the microsurgery saw laterally. The mechanism may be designed such that the saw engaging means comprises a boss extending upwardly and distally from the main way block portion having formed therethrough a passage defined at the distal end by an oval opening having the major axis parallel to the plane in which the way block moves laterally and saw engaging structure accessible through said passage.

A rotary-to-lateral movement converting mechanism is disclosed and claimed which comprises a concentric eccentric rotor forming a main rotary portion, a concentric rotary portion and an eccentric rotary portion, having a motor operably connected for driving the concentric-eccentric rotor, means mounting the concentric-eccentric for rotation on the main rotary portion, and a way assembly mounted for reciprocal lateral motion perpendicular to the axis of the main rotary portion of the concentric-eccentric rotor. The way assembly comprises a body having formed therein a generally oval opening having opposed side walls and the rotor is so constructed and disposed that the eccentric rotary portion engages at alternating intervals the respective sides of a generally oval opening in the way body for moving the way body in reciprocal motion laterally. The mechanism may be, but is not necessarily, constructed, dimensioned and configured to drive an elongate cervical saw having a proximal end adapted to engage drive means and a distal end adapted to cut bone, tissue and the like. In this form, the mechanism includes means for engaging the proximal end of the cervical saw and causing lateral movement thereof.

In one form, the invention is viewed as comprising a microsurgery saw support assembly constructed and adapted to support an elongate generally cylindrical cervical or other microsurgery saw having cutting means at the distal end and moving mechanism engaging means at the proximal end. The invention thus viewed comprises a generally cylindrical hand grip member, a pivot supported for pivotal motion inside the hand grip member, and a microsurgery saw blade support comrising a generally cylindrical member and retaining means for receiving and selectively securing and releasing the microsurgery saw. The pivot is, in the preferred form of this embodiment, an omni-directional pivot ball and means supporting the ball for pivotal movement. The retaining means preferably, but not necessarily, comprises at least one detent and one retaining ball in the detent. Generally, a pair of detents carrying a pair of balls is used, but one, two, three or more may be used.

In a more encompassing view, the invention is a drive mechanism for supporting and driving an elongate, generally cylindrical microsurgical saw for performing cervical and other microsurgical procedures. Thus, the invention comprises a rotary-to-lateral motion converting assembly comprising concentric-eccentric rotor so constructed and arranged as to form a central main rotor portion, a proximal concentric drive shaft portion and an eccentric distal drive shaft portion, all driven by a motor through means operably connecting the motor to the concentric-eccentric rotor for rotating the same. A way block mounted for reciprocal, lateral travel is engaged by the eccentric drive shaft portion for driving the same in response to drive power from the motor is thus driven reciprocally laterally to thereby convert the rotary motion of the motor through the concentric-eccentric rotor to lateral motion of the way block. A microsurgery saw support assembly constructed and adapted to support an elongate generally cylindrical microsurgery saw having cutting means at the distal end and means at the proximal end for engaging the way block is positioned adjacent the way block. The microsurgery saw support assembly comprises a generally cylindrical hand grip member, a pivot supported for pivotal motion inside the hand grip member, and a microsurgery saw blade support comprising a generally cylindrical member and retaining means for receiving and selectively securing and releasing the microsurgery saw. The way block comprises saw engaging means for moving the proximal end of the microsurgery saw laterally, which may include saw engaging structure comprising a pin for engaging in a slot in the proximal end of the microsurgery saw.

The invention is, thus, in one form a microsurgery saw support and drive mechanism so constructed, dimensioned and configured as to be adapted to drive an elongate microsurgery saw having a proximal end adapted to engage drive means and a distal end adapted to cut bone, tissue and the like, comprising rotary-to-lateral movement converting mechanism comprising a concentric-eccentric rotor forming a main rotary portion, a concentric rotary portion and an eccentric rotary portion, a motor operably connected for driving the concentric-eccentric rotor, means mounting the concentric-eccentric for rotation on the main rotary portion, a way assembly mounted for reciprocal lateral motion perpendicular to the axis of the main rotary portion of the concentric-eccentric rotor, the way assembly comprising a body having formed therein a generally oval opening having opposed side walls, the rotor being so constructed and disposed that the eccentric rotary portion engages at alternating intervals the respective sides of a generally oval opening in the way body for moving the way body in reciprocal motion laterally, a microsurgery saw support assembly constructed and adapted to support an elongate microsurgery saw having cutting means at the distal end and means at the proximal end for engaging the way block, and means on the way block for engaging the proximal end of the microsurgery saw and causing lateral movement thereof. The microsurgery saw support assembly may comprise an elongate hand grip member, a pivot supported for pivotal motion inside the hand grip member, and a microsurgery saw blade support comprising an elongate saw receiving member for receiving therein the microsurgery saw and retaining means for receiving and selectively securing and releasing the microsurgery saw.

A microsurgery saw is also disclosed, comprising an elongate structure having a proximal end and a distal end of from about three to about 20 cm. in length and a diameter of from about three to about 10 mm, a cutting tool formed proximate the distal end of the elongate structure generally perpendicular to the longitudinal axis thereof, and engaging and retaining means formed proximate the proximal end of the elongate structure. The engaging means may comprise a slot transversely formed in the proximal end of the elongate structure, and the retaining means may comprise an annular groove circumscribing the elongate structure proximate the proximal end thereof. The elongate structure preferably is generally cylindrical along a major portion of the length thereof.

The invention comprises the combination of drive means for producing rotary motion, rotary-to-lateral converting means operatively driven by the drive means, saw support means for pivotally supporting a microsurgery saw operatively connected to the converting means for transmitting lateral drive motion to the microsurgery saw, drive casing means surrounding and positioning the drive means and saw support casing means surrounding and positioning the saw support means. In a preferred embodiment, the drive casing means and the saw support casing means are generally cylindrical, each having a generally central axis, the casing means being secured to each other such that the angle between the axes of the casing means is about fifteen degrees, the exact angle not being extremely critical, angles of from about ten to about 30 degrees being acceptable, though the fifteen degree angle is strongly preferred.

These and other important structural and functional features of the invention are more clearly set forth in the specification, in which only one exemplary embodiment is described and in the drawings, it being expressly pointed out that only the currently known best mode is described though many variations are possible within the scope of the invention.

BRIEF DESCRIPTION OF THE DRAWINGS

FIG. 3 is a continuation, to the right as viewed, of the mechanism of FIG. 2, some components being duplicated for clarity of presentation, showing the cervical saw blade support and holder portion of this invention, the cervical saw being shown in position for FIGS. 4A and 4B show the retaining and release positions of the cervical saw blade support and holder with the saw therein.

FIG. 5 is a partial view, in cross section showing some details of the omni-directional pivot ball support for th saw.

DESCRIPTION OF THE PREFERRED EMBODIMENT

In describing the following embodiment, which is currently the preferred embodiment and the best mode known to the inventor, it is to be clearly understood that the structures and interrelationships are described in detail as an example of the invention and not as the only form of the invention; indeed, many forms are possible for the invention and many substitutions and variations can be made without departing from the spirit and scope of the invention. For example, the casing for the cervical saw is convenient but of no criticality insofar as the invention is concerned. Likewise, any light-weight motor can be used. For example, fluid turbines may be used in lieu of electric motors, such as, by way of example only, the fluid turbine motors commonly used in dental tools. Except as specifically claimed and limited in the claims, the interconnections and configurations are merely exemplary of a great variety of variations which can be made without departing from the invention.

An overall description of the invention will be provide first, with details of certain mechanisms and relationships being described thereafter.

Figure 2:
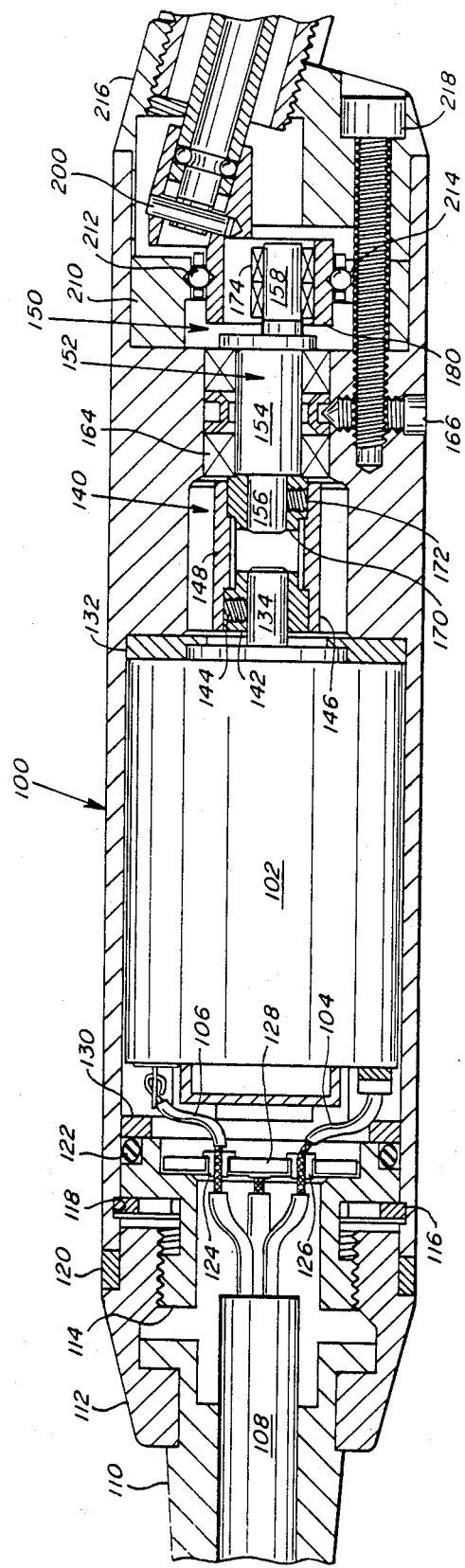
FIG. 2 is a side view in cut-away and cross section of the main cylindrical part of the drive and the rotary-to-lateral motion conversion mechanism of the present invention.
Figure 1:
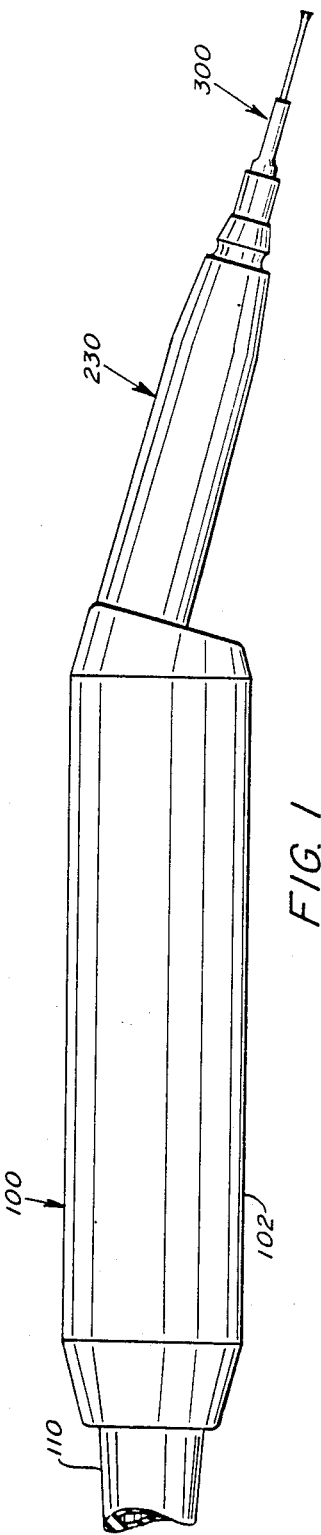
FIG. 1 is a side view of the cervical saw drive of this invention.

The cervical saw drive, generally shown in FIG. 1 and shown in greater detail in FIG. 2, comprises a casing 100 which is a generally elongate cylinder having external structure for providing gripping surfaces, to permit the surgeon to grip the drive during use, and internal structure for receiving and positioning the drive motor 102 and the interconnected drive mechanisms.

The power for driving the saw, in this example, is an electric motor 102 which received electrical energy from wires 104 and 106 of cord 108 which is provided with a plug and adapted to plug into any compatible electrical energy source. The cord 108 is surrounded by a strain relief sleeve 110 the proximal end of which is attached to the casing 100 by an internally threaded retaining sleeve 112 which, in turn, is held in the sleeve 100 by externally threaded sleeve 114, which is secured by retaining ring 116 which seats in groove 118 which is formed in the interior of sleeve 100. Ring 120 surrounds the proximal, internally threaded end of retaining sleeve 112 assuring a tight, substantially moisture-proof seal between the threads of the retaining sleeve 112 and the threads of externally threaded sleeve 114. The proximal end of the externally threaded sleeve 114 forms an annular land upon which an O-ring 122 rests, the O-ring 122 forming a seal between the interior surface of sleeve 100 and sleeve 114. The strain relief covering 110 is formed of rubber or other resilient polymer to permit the cord to bend gradually and prevent sharp bends which would unduly strain the cord. The internally threaded sleeve 112, the strain relief covering 110, the externally threaded sleeve 114 and the O-ring 122 form a substantially water tight seal for preventing moisture from entering the sleeve.

The power providing conduits 104 and 106 extend through grommets 124 and 126 in passages through insulator disc 128 and are attached to the input terminals of motor 102 according to conventional electrical wiring procedures. The insulator disk 128 is disposed against a shoulder formed in the proximal portion of the externally threaded sleeve 114 and in spaced relationship with the distal end of motor 102 by a spacer ring 130. The proximal end of the motor 102 is held in position and sealed by a retaining and sealing ring 132. The spacer rings 130 and 132 secure the motor 102 in insulated, fixed position in the sleeve 102. The combination of these seals prevents moisture from entering the portion of the sleeve occupied by the electrical connections and motor under most use environmental conditions, and mounts the motor for operation in the sleeve, but does not necessarily seal the motor sufficiently to permit immersion of the drive.

The rotationally driven shaft 134 of the motor 102 is operationally connected to a drive coupling mechanism indicated generally at 140 comprising sleeve 142 secured to the shaft 144 by a set screw 146 and engages internally splined or geared coupling sleeve 148.

Figure 6:
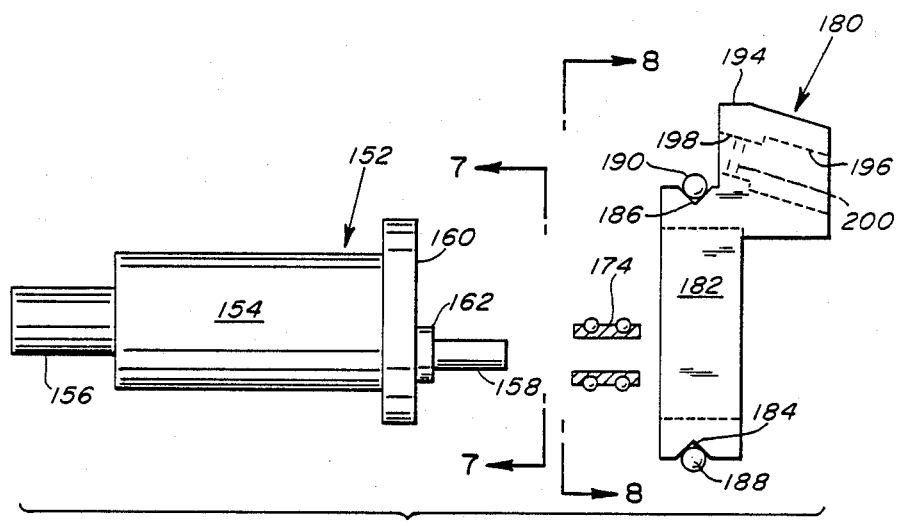
FIG. 6 is a partial, exploded view, partially schematic, of the rotary-to-lateral motion conversion mechanism of t present invention.
Figure 7:
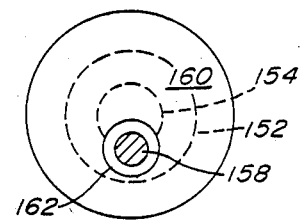
FIG. 7 is an end view, taken along Lines 7—7 of FIG. 6, showing the concentric-eccentric rotor of the rotary-to-late motion conversion mechanism.
Figure 8:
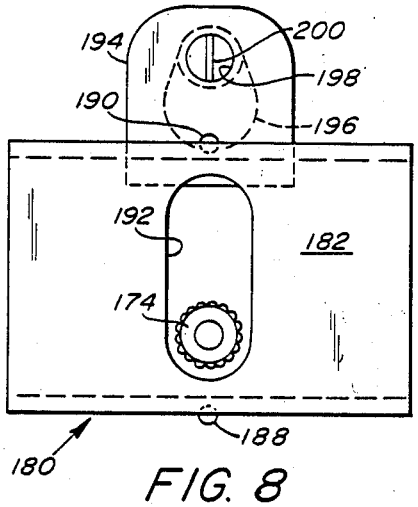
FIG. 8 a face view, taken along Lines 8—8 of FIG. 6, of the way block assembly of this invention.

A rotary-to-lateral motion converting assembly indicated generally at 150 in FIG. 2, and shown in greater, somewhat schematic, detail in FIGS. 6–8 inclusive, to which reference is now made, is disposed in the proximal portion of the sleeve 100. A concentric-eccentric rotor 152 comprising a central main rotor portion 154, a proximal concentric drive shaft portion 156 and an eccentric distal drive shaft portion 158 and may conveniently include a flange 160 on the main rotor portion and a shoulder 162 on the eccentric drive shaft is mounted for rotation in the sleeve by a double-ball bearing assembly 164 conveniently held in place by set screw 166. The distal drive is operably connected to the motor 102 by means of an external spline gear 170 mounted by a set screw 172 to the concentric drive shaft portion 156 of the concentric-eccentric rotor 152 and an internal spline gear sleeve 148 which engages the corresponding spline gear 142 on the output shaft 144 of the motor 102. The concentric-eccentric rotor 152 is thus rotatably driven by the motor 102.

The eccentric drive shaft 158 carries a ball bearing assembly 174 which interacts with the lateral way block 180 to convert the rotary motion of the concentric-eccentric rotor to lateral motion of the way block in the manner now described.

Figure 9:
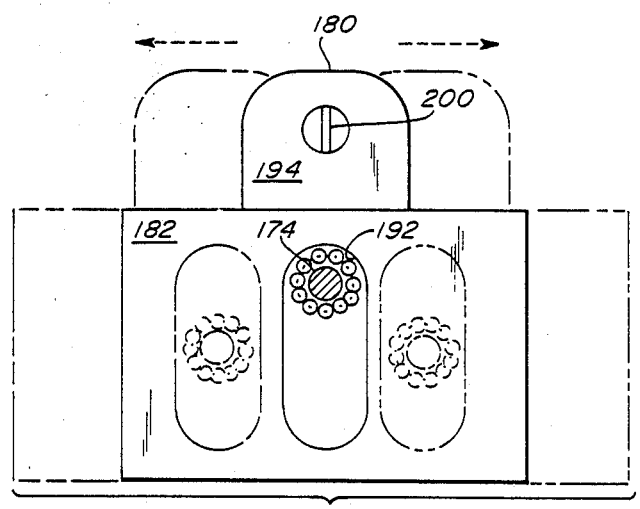
FIG. 9 is a schematic view showing the way block and the means for laterally driving the same and depicting the lateral movement of the same.

The way block 180 comprises a generally rectangular main block portion 182, though the configuration is not critical, provided, in the preferred embodiment with V-shaped ways 184 and 186 which are adapted to engage balls 188 and 190 which movably support the bottom and the top, respectively, of the way block 180 for lateral movement in a plane perpendicular to the axes of the concentric-eccentric rotor 152. A generally oval aperture 192 is formed in the main block portion 182 having, in the preferred form, generally straight sides and generally arcuate ends, though the shape is not critical so long as it is generally oval. As the concentric-eccentric rotor 152 is caused to rotated by operation of the motor 102, the eccentric shaft portion thereof 158, through bearing 174, engages the side walls of the aperture 192, first one side moving the way block 180 to the right then the other side moving the way block 180 to the left as shown in FIG. 9.

The way block 180 also comprises, in this preferred embodiment, saw engaging means which function to move the proximal end of the cervical saw laterally, as will be described. The saw engaging means comprises a boss 194 extending upwardly and distally from the main way block portion 182 having formed therethrough a stepped passage defined at the distal end by an oval opening 196 having the major axis parallel to the plane in which the way block moves laterally and a smaller opening 198 which is traversed by a saw engaging pin 200. It is pointed out, however, that any means of engaging and moving the proximal end of the cervical saw laterally with the lateral movement of the way block can be used and that the use of the apertured boss is simply one convenient means for accomplishing this function. It will also be noted that the aperture extends through the boss only because this a convenient and inexpensive way to machine the saw engaging means and that the smaller opening 198 need not extend through the boss.

To review, the rotary-to-lateral movement converting mechanism 150 of this invention comprises concentric-eccentric rotor 152 driven by the motor and mounted for rotation on main rotary portion 154 coaxial with or on a parallel axis with the axis of the motor 102 (though this axial relationship is not critical) having an eccentric rotary portion 158 which lies on an axis parallel to the main axis (the axis through the main rotary portion 154) but offset therefrom which engages at alternating intervals the sides of a generally oval vertically oriented opening 192 in the main portion of the way block 180. The major axis of the oval opening 192 is perpendicular to both the direction of lateral movement and the main axis of the concentric-eccentric rotor 152, thus the eccentric rotary portion 158 moves the way block 180 laterally and not vertically, as the eccentric rotary portion 158 does not, engage the ends of the oval opening 192. The way block 180 includes means for engaging the proximal end of the cervical saw and causing lateral movement thereof. In the foregoing summary, structures which are necessary for long-term reliable operation but not important to the concept of the rotary-to-lateral movement converting mechanism 150 have not been mentioned for the sake of simplicity.

Way mounting ring 210 having formed therein a pair of ways 212 and 214 which, respectively, receive balls 188 and 190 which, as previously described, support way block 180 for reciprocal lateral movement. Thus, the mounting ring 210 along with the balls 188 and 190 form support means for and permitting reciprocal lateral movement of the way block 180. Way mounting ring 210 and a proximal end closure block 216 are held in place closing the proximal end of the sleeve, except as will be described, by retaining screw 218 which is screwed into a matching threaded aperture in the sleeve. These last described mechanisms are not critical as to shape or configuration and any convenient support for the way block 180 and closure for the sleeve may be used.

While the mechanism thus far described can be use for many purposes, it is used, in this preferred embodiment, in connection with a cervical saw and cervical saw support assembly. The cervical saw support assembly 230, best shown in FIGS. 3, 4 and 5, to which reference is now made, comprises a generally cylindrical support sleeve 232 one end of which is threaded and is threadably received in mating threads in the proximal end closure 216, in this preferred embodiment, at an angle of about 15 degrees, i.e. the axis of the support sleeve 232 is at an angle of about 15 degrees with respect to the axis of the sleeve 202. A generally cylindrical hand grip member 234 is threadably engaged external of the sleeve 232 by mating threads 236 surrounding the same and extending beyond the end of the sleeve 232, the internal structure including a generally right cylindrical surface 240 terminating at a shoulder 240 formed by a smaller conical internal diameter 242 proximate the distal end thereof, the internal conical portion 242 expanding from the shoulder 242 to the distal tip 244 of the hand grip member 234, a generally cylindrical external surface 246 and a tapered external tip portion 248 forming a surface of size and texture convenient to permit gripping by the surgeon during use.

Disposed inside the hand grip member 234 is an omnidirectional pivot ball 250 having a cylindrical passage therethrough supported for pivotal motion inside the hand grip member 234 by pivot bearings 252 and 254 and resiliently biased by spring 256 toward the proximal end of the generally cylindrical hand grip member 234 against the distal-most end of the support sleeve 232 and an indexing ring 258 which has depressions which engage at two positions detents on ring 260 and inside the distal end portion of the support sleeve 232. The detent arrangement of the engagement of indexing ring 258 and detent ring 260 provides a tactile "feel" to the surgeon as he turns the blade locking assembly to indicate when the saw is locked in place. The spacer ring 260 abuts against shoulder 262 formed in the support sleeve 232, the entire supporting means for the omni-directional pivot ball 250 pivotally supporting the pivot ball about midway or slightly distal of midway of the cervical saw support assembly 230.

The distal end of the cervical saw support assembly 230 is partially sealed by a resilient sleeve 264 the proximal end of which is so structured and configured as to form a flange 266 which is held in fluid tight relation to the shoulder 240 by the biasing spring 256, which have been previously described, the distal end of the resilient sleeve 264 resiliently gripping a distal cylindrical support and sealing tube 268 rests against the distal end of the omni-directional pivot ball 250.

Cervical saw blade support and holder 270 comprises a generally cylindrical member which conveniently is so constructed as to form an external shoulder 272 which abuts in sealing and position fixing relationship with the sealing ring 258, previously described, and is generally cylindrical interiorly. Adjacent the proximal end of the Cervical saw blade support and holder 270 apertures 274 and 276 receive, respectively, retaining balls 278 and 280 the retaining balls being held relatively loosely in the apertures to permit them to extend inwardly of the Cervical saw blade support and holder 270 or to extend outwardly thereof, selectively according to the force exerted thereupon. The proximal end portion of the Cervical saw blade support and holder 270 is adapted to be and, in use, is received in the oval aperture 196, extending distally therefrom through the omni-directional pivot ball 250, being snugly rotatable in the oval aperture 196 and in the sleeve 268 and pivotally mounted by the omni-directional pivot ball 250.

In use, a cervical saw 300 is received and retained in the Cervical saw blade support and holder 270. The cervical saw comprises an elongate cylindrical shaft 302 having formed in the proximal end thereof engaging means conveniently in the form of a slot 304 perpendicular of the axis of the shaft 302 for engaging the pin 200 which moves reciprocally as part of the way block 180 and adjacent thereto an annular groove 306 which is formed in the cylindrical portion 302 for receiving the retaining balls 278 and 280 and a distal cutter tip 308 which may be straight or bent or curved and may have any type of teeth, cutting edges, serrations, etc. thereon.

The structure, function and mode of operation of the rotary-to-lateral motion conversion mechanism 150 has been described. The mechanism thus described and the drive, support and related mechanisms act to drive the distal cutting tip of the cervical saw 300 laterally in a reciprocating arcuate path, though the radius of the art of movement is so large that arcuate shape of the cut can largely be disregarded.

In operation, the way block 180 is moved laterally by the motor 102 through the rotary-to-lateral motion conversion mechanism 150 as described, and thus moves the proximal end of the cervical saw 300 laterally, the slotted proximal end operatively engaging the pin 200 as the way block 180 reciprotates laterally back and forth. The cervical saw 300 is caused thereby to pivot on the omni-directional pivot ball 250 thus causing the distal cutting tip to reciprocate laterally in a plane substantially perpendicular to the plane in which the way block 180 reciprocates. Lateral reciprocation of the cutter tip 308 is operative to cut or saw bone or other body structure.

The present invention can be made of many materials and in many forms, the form illustrated and described above being merely exemplary.

Figure 10:
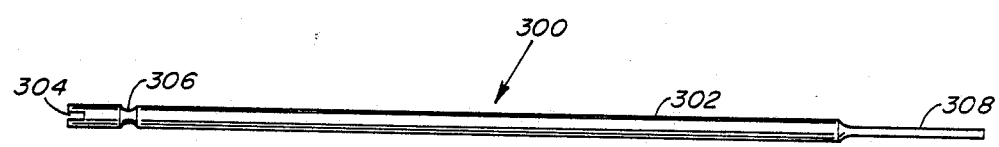
FIG. 10 is a side view of a microsurgery saw of the type which be used with this invention.
Figure 11:
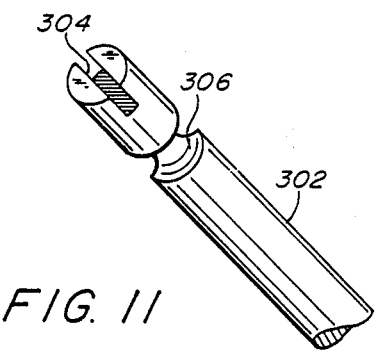
FIG. 11 is an enlarged, perspective view of the proximal end portion of the saw depicted in FIG. 10.

In a typical, preferred form, the microsurgery saw is an elongate, generally cylindrical saw having a diameter of about 4 mm, but the diameter may range from about 2 or 3 mm to as much as 6 or 8 mm, and a length typically of about 10 cm, though the length may be from about 3 or 4 up to about 15 or 20 cm. The cutting edge of the saw is typically about 6 to 8 mm in width, but may be from 2 to 3 mm up to about 25 mm or more, typically. As shown in FIGS. 10 and 11, the microsurgery saw 300 preferably comprises an elongate cylindrical shaft portion 302 having formed at the proximal end, drive engaging means such as slot 304 and retaining means such as the annular groove 306 and a cutting tool portion 308.

Industrial Application

This invention is useful in orthopedic and other surgical procedures.

What is claimed is:

1. A rotary-to-lateral motion converting assembly comprising concentric-eccentric rotor (152) so constructed and arranged as to form a central main rotor portion (154), a proximal concentric drive shaft portion (156) and an eccentric distal drive shaft portion (158), a motor (102), means operably connecting the motor (102) to concentric-eccentric rotor (152) for rotating the same, a way block (180) mounted for reciprocal, lateral travel, the eccentric drive shaft portion so disposed and constructed as to engage the lateral way block (180) for driving the same in response to drive power from the motor reciprocally laterally to thereby convert the rotary motion of the motor through the concentric-eccentric rotor to lateral motion of the way block, the way block being constructed and configured to drive a cervical saw and comprising saw engaging means for moving the proximal end of the cervical saw laterally, the saw engaging means comprising a boss (194) extending distally from he main way block portion (182) having formed therethrough a passage defined at the distal end by an oval opening (196) having the major axis parallel to the plane in which the way block moves laterally and saw engaging structure (200) accessible through said passage.

2. The mechanism of claim 1 wherein the way block (180) comprises a generally rectangular main block portion (182) having formed thereon way (184,186) constructed and disposed to movably support the way block (180) for lateral movement in a plane generally perpendicular to the axes of the concentric-eccentric rotor (152).

3. The mechanism of claim 2 wherein the way block (180) is so constructed and configured as to define a generally oval aperture (192) in the main block portion (182) for receiving the eccentric shaft (158) of the concentric-eccentric rotor (152), the aperture (182) being so formed and configured as define side walls which are operably engaged alternately by the eccentric shaft portion thereof (158) first on one wall for moving the way block (180) in one direction laterally and then on the other wall for moving the way block 180 in the other direction laterally.

4. The mechanism of claim 3 constructed and configured to drive a cervical saw, wherein the saw engaging means comprises means for receiving and moving the proximal end of the cervical saw laterally, and wherein the saw engaging boss (194) extends upwardly and distally from the main way block portion (182).

5. A drive mechanism for supporting and driving an elongate microsurgical saw which comprises an elongate shaft having an axis and proximal and distal ends and a planar saw having teeth extending substantially parallel to the shaft axis for performing cervical and other microsurgical procedures, comprising, in combination: a generally axially aligned rotary-to-lateral motion converting assembly of substantially constant diameter comprising a concentric-eccentric rotor (152) so constructed and arranged as to form a central main rotor portion (154), a proximal concentric drive shaft portion (156) and an eccentric distal drive shaft portion (158), a motor (102), means operably connecting the motor (102) to concentric-eccentric rotor (152) for rotating the same, a way block (180) mounted for reciprocal travel laterally within said substantially constant diameter, the eccentric drive shaft portion so disposed and constructed as to engage the lateral way block (180) for driving the same in response to drive power from the motor reciprocally laterally to thereby convert the rotary motion of the motor through the concentric-eccentric rotor to lateral motion of the way block, and a microsurgery saw support assembly (230) constructed and adapted to support the elongate microsurgery saw comprising a pivot (250) for supporting the microsurgery saw blade intermediate the ends thereof, and retaining means for receiving and selectively securing and releasing the microsurgery saw, the way block comprising a boss extending therefrom having an opening therethrough and an engaging pin for receiving and engaging the proximal end of the microsurgery saw and moving said proximal end and, through said pivot, moving the distal end of the saw generally laterally to the axis of the rotary-to-lateral motion converting assembly.

6. The mechanism of claim 5 wherein the way block (180) comprises a generally rectangular main block portion (182) having formed thereon ways (184,186) constructed and Disposed to movably support the way block (180) for lateral movement in a plane generally perpendicular to the axes of the concentric-eccentric rotor (152).

7. The mechanism of claim 6 wherein the way block (180) is so constructed and configured as to define a generally oval aperture (192) in the main block poriton (182) for receiving the eccentric shaft (158) of the concentric-eccentric rotor (152), the aperture (182) being so formed and configured as define side walls which are operably engaged alternately by the eccentric shaft portion thereof (158) first on one wall for moving the way block (180) in one direction laterally and then on the other wall for moving the way block (180) in the other direction laterally.

8. The mechanism of claim 7 wherein the way block (180) comprises saw engaging means for moving the proximal end of the microsurgery saw laterally.

9. A drive mechanism for supporting and driving an elongate, generally cylindrical microsurgical saw for performing cervical and other microsurgical procedures, comprising, in combination: a rotary-to-lateral motion converting assembly comprising concentric-eccentric rotor (152) so constructed and arranged as to form a central main rotor portion (154), a proximal concentric drive shaft portion (156) and an eccentric distal drive shaft portion (158), a motor (2), means operably connecting the motor (102) to concentric-eccentric rotor (152) for rotating the same, a way block (180) mounted for reciprocal, lateral travel, the eccentric drive shaft portion so disposed and constructed as to engage the lateral way block (180) for driving the same in response to drive power from the motor reciprocally laterally to thereby convert the rotary motion of the motor through the concentric-eccentric rotor to lateral motion of the way block, saw engaging means on the way block, a nd a microsurgery saw support assembly (230) constructed and adapted to support an elongate generally cylindrical microsurgery saw having cutting means at the distal end and means at the proximal end for engaging the way block, the microsurgery saw support assembly comprising a pivot (250) and a microsurgery saw blade support (270) comprising a generally cylindrical member and retaining means for receiving and selectively securing and releasing the microsurgery saw, the saw engaging means comprising a boss (194) extending upwardly and distally from the main way block portion (182) having formed therethrough a passage defined at the distal end by an oval opening (196) having the major axis parallel to the plane in which the way block moves laterally and saw engaging structure (200) accessible through said passage.

10. The mechanism of claim 9 wherein the saw engaging structure comprises a pin for engaging In a slot in the proximal end of the microsurgery saw.

11. The microsurgery saw support assembly of claim 9 wherein the pivot is an omni-directional pivot ball and means supporting the ball for pivotal movement.

12. The microsurgery saw support assembly of claim 9 wherein the retaining means comprises at least one detent and one retaining ball in the detent.

* * * * *